US010258922B2

(12) United States Patent
Hsieh

(10) Patent No.: US 10,258,922 B2
(45) Date of Patent: Apr. 16, 2019

(54) DEVICE FOR DEODORIZATION AND DISINFECTION

(71) Applicant: Xetin Co., Ltd., Taipei (TW)

(72) Inventor: Ying-Yi Hsieh, Taipei (TW)

(73) Assignees: XETIN CO., LTD, New Taipei (TW); Ying-Yi Hsieh, Taipei (TW)

( * ) Notice: Subject to any disclaimer, the term of this patent is extended or adjusted under 35 U.S.C. 154(b) by 0 days.

(21) Appl. No.: 15/700,164

(22) Filed: Sep. 10, 2017

(65) Prior Publication Data

US 2019/0076779 A1 Mar. 14, 2019

(51) Int. Cl.
| | | |
|---|---|---|
| *H05K 7/20* | (2006.01) |
| *A61L 9/015* | (2006.01) |
| *C01B 13/11* | (2006.01) |
| *B01D 53/34* | (2006.01) |
| *C02F 1/78* | (2006.01) |

(52) U.S. Cl.
CPC ............... *B01D 53/34* (2013.01); *C02F 1/78* (2013.01)

(58) Field of Classification Search
CPC .... B03C 3/68; B03C 3/32; B03C 3/36; B03C 3/011; B03C 3/155; B03C 3/88; B03C 2201/06; B03C 3/74; B03C 3/82; A61L 9/015; A61L 9/22; A61L 2/202; A61L 2209/212; A61L 2/183; A61L 2209/134; A61L 2/0094; A61L 9/12; A61L 9/122; F24F 2003/1682; F24F 2003/1685; F24F 13/20; F24F 13/28; F24F 3/16; F24F 3/1603; F24F 11/77; F24F 2221/22; B01D 2251/104; B01D 46/2411; B01D 46/44; B01D 53/8675; H01T 19/00; G01N 21/51; Y10T 436/206664; H05H 2001/481; F04D 29/703; H01L 23/467; B60H 3/0071; H05K 7/20172; H05K 7/20909; Y02A 50/21; Y10S 261/88; A61M 16/105; A62B 7/10; F01N 3/0821; Y02B 30/563; Y02B 30/78

See application file for complete search history.

(56) References Cited

U.S. PATENT DOCUMENTS

| | | | | |
|---|---|---|---|---|
| 5,407,469 A | * | 4/1995 | Sun .......................... | B03C 3/011 361/226 |
| 5,484,472 A | * | 1/1996 | Weinberg ................. | A61N 1/44 323/903 |

(Continued)

*Primary Examiner* — James Wu
*Assistant Examiner* — Michael A Matey
(74) *Attorney, Agent, or Firm* — Bruce Stone LLP; Joseph Bruce

(57) ABSTRACT

A device for deodorization and disinfection is provided. The aforementioned device includes a supporter, a fan module, a high voltage generating module, a controlling circuit, a battery module, and a cover body used to contain aforementioned elements. Aforementioned supporter includes a first supporting portion, a second supporting portion, and a third supporting portion. The fan module attaches to a setting plane of the first supporting portion. The high voltage generating module is configured at the third supporting portion and below the fan module, and a corona generator of the high voltage generating module is configured at an air outlet of the fan module. The battery module is configured at a holding space formed by the second supporting portion and the third supporting portion. The controlling circuit makes the battery module provide power to the fan module and the high voltage generating module.

7 Claims, 5 Drawing Sheets

(56) References Cited

U.S. PATENT DOCUMENTS

| | | | | |
|---|---|---|---|---|
| 5,667,564 A | * | 9/1997 | Weinberg | A61L 9/22 323/903 |
| 2003/0175171 A1 | * | 9/2003 | Yamamoto | A01M 1/2033 422/124 |
| 2008/0047433 A1 | * | 2/2008 | Ouyang | B03C 3/155 96/24 |
| 2010/0033891 A1 | * | 2/2010 | Orihara | B08B 1/00 361/231 |
| 2014/0131459 A1 | * | 5/2014 | Dorendorf | F24F 11/0001 236/49.3 |
| 2016/0367712 A1 | * | 12/2016 | Robert | A61L 9/22 |
| 2017/0202993 A1 | * | 7/2017 | Huang | A61L 9/015 |
| 2017/0321720 A1 | * | 11/2017 | Park | F04D 29/703 |

* cited by examiner

DEVICE FOR DEODORIZATION AND DISINFECTION

BACKGROUND OF THE INVENTION

1. Field of the Invention

The present invention relates to a device for deodorization and disinfection, in particular, to a device for deodorization and disinfection capable of having a small volume and being easy to be placed anywhere for use by configuring inner positions for modules.

2. Description of the Prior Art

Since ozone has the properties of colorlessness and high oxidation, the high oxidation of ozone was used mostly by prior art to conduct oxidation reaction on injurious substances such as bacteria, peculiar smell so as to achieve the purpose of eliminating peculiar smell and killing bacteria.

However, the current generator for ozone is too large, and acquires operation power supply through the electrical wire, so the extant ozone generators mostly being installed in industrial environments. For the purpose of deodorization and disinfection in a small space to be achieved only by spaying chemical agents such as deodorant, fungicide when in a situation where the electrical wire cannot be arranged. Therefore, it is essential for popularizing the ozone generator applications to solve such problems of the ozone generator being too large and how to power by the electrical wire.

In summary, how to provide a scheme of effectively reducing the volume of ozone generator and supplant of powering through electrical wire is a technical problem needed to be addressed by the field.

SUMMARY OF THE INVENTION

To solve aforementioned problems, the purpose of the present invention provides a small device for deodorization and disinfection that can be placed in various locations.

To achieve above purpose, the present invention proposes a device for deodorization and disinfection. The aforementioned device includes a supporter, a fan module, a high voltage generating module, a controlling circuit, a battery module, and a cover body. The aforementioned supporter includes a first supporting portion, second supporting portion, third supporting portion and base, wherein one end of the first supporting portion connected with the second supporting portion to form a first angle, and one part of the second supporting portion connected the third supporting portion to form a second angle, one end of the third supporting portion connected with the base. The aforementioned fan module attaches to a setting plane of the first supporting portion. The aforementioned high voltage generating module is configured at the third supporting portion and below the fan module, wherein a corona generator of the high voltage generating module is configured at an air outlet of the fan module. The aforementioned battery module is connected with the fan module and high voltage generating module and configured at a holding space formed by the second supporting portion and the third supporting portion. The aforementioned controlling circuit is electrically connected with the fan module, the high voltage generating module, and the battery module so as to configure an operation of the fan module and the high voltage generating module. The aforementioned cover body is used to cover the supporter, fan module, high voltage generating module, controlling circuit and battery module.

In summary, compared with conventional device for deodorization and disinfection, the present invention, by configuring a supporter structure inside the device for deodorization and disinfection, can effectively diminish the entire volume of the device and solve the problem of powering through the inner battery module, thus allowing the user to have more flexible options on mounting environment for the device.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

DETAILED DESCRIPTION OF THE PREFERRED EMBODIMENT

The following description is about embodiments of the present invention; however it is not intended to limit the scope of the present invention.

Figure 1:
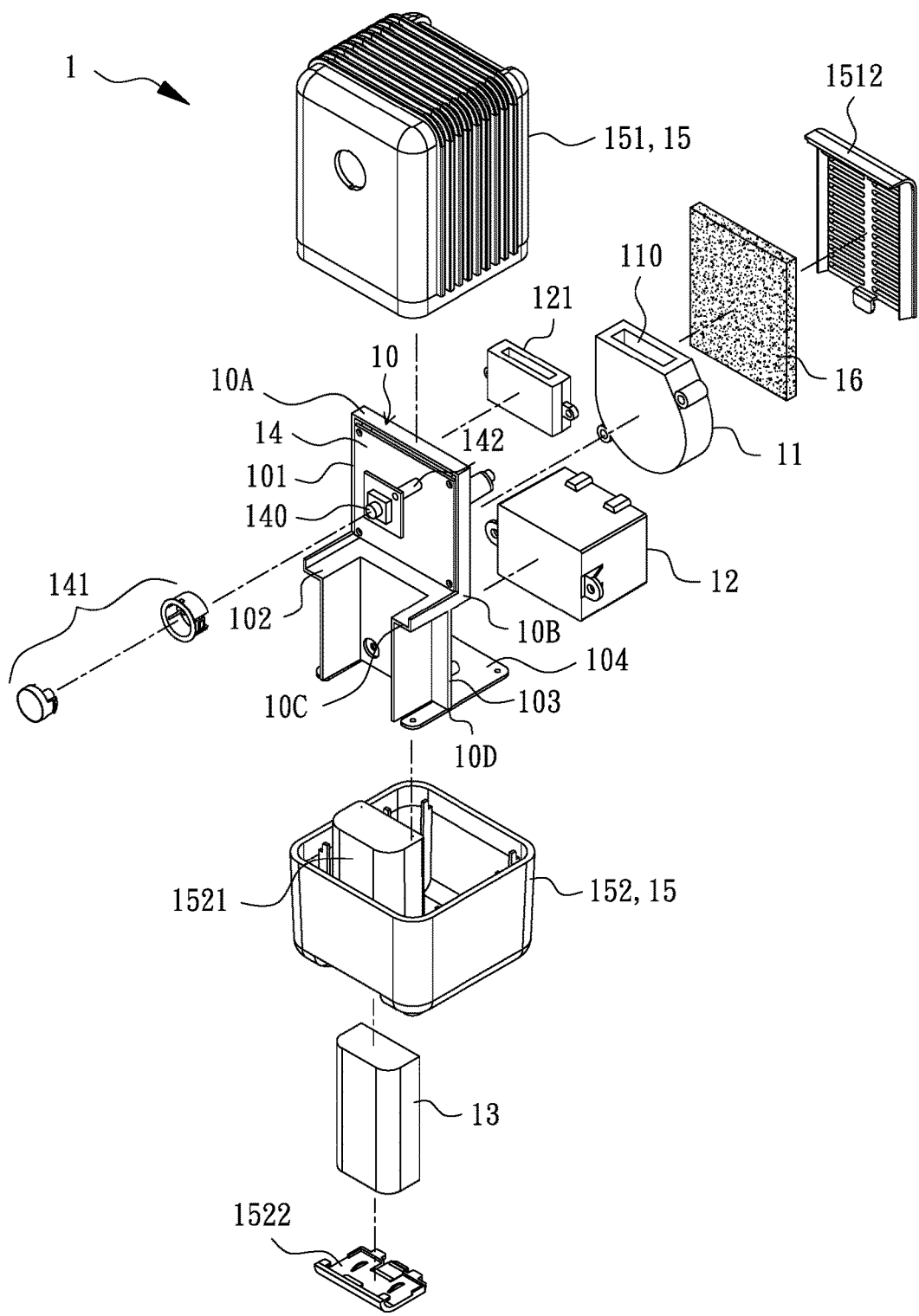
FIG. 1 is a stereoscopic exploded view of one embodiment of the device for deodorization and disinfection in the present invention.

With reference to FIG. 1, a stereoscopic exploded view of one embodiment of the device 1 for deodorization and disinfection in the present invention is shown. The aforementioned device 1 for deodorization and disinfection mainly comprises a supporter 10, a fan module 11, a high voltage generating module 12, a battery module 13, a controlling circuit 14 and a cover body 15. With common reference to FIG. 2, a cross section view of the device 1 for deodorization and disinfection is shown. The aforementioned supporter 10 includes a first supporting portion 101, second supporting portion 102, third supporting portion 103 and base 104, wherein one end of the first supporting portion 101 is connected with the second supporting portion 102 to form a first angle, and one part of the second supporting portion 102 is connected the third supporting portion 103 to form a second angle, one end of the third supporting portion 103 connected with the base 104. The aforementioned first angle and second angle exclude 0 degree and 180 degree. Preferably, the aforementioned first angle and second angle value may be 90 degree or approximately be 90 degree (e.g. E10 degree). In detail, the aforementioned supporter 10 forms the first supporting portion 101 between a first end 10A and a second end 10B along a first axial direction VD, then the first supporting portion 101 forms the second supporting portion 102 between the second end 10B and a third end 10C along a second axial direction and forms the third supporting portion 103 between one part of the second supporting portion 102 and a fourth end 10D along the first axial direction VD.

The aforementioned fan module 11 attaches to a setting plane of the first supporting portion 101. And the high voltage generating module 12 is configured at a setting plane of the third supporting portion 103 and below the fan module 11, wherein a corona generator 121 connected with the high voltage generating module 12 is configured at an air outlet 110 of the fan module 11. The aforementioned battery module 13 is connected with the fan module 11 and high voltage generating module 12 and the battery module 13 is configured at a holding space formed by the second supporting portion 102 and the third supporting portion 103. The aforementioned controlling circuit 14 is electrically connected with the fan module 11, the high voltage generating module 12, and the battery module 13 so as to configure an operation of the fan module 11 and the high voltage generating module 12. The aforementioned cover body 15 is used to cover the supporter 10, fan module 11, high voltage generating module 12, controlling circuit 14 and battery module 13.

Figure 3:
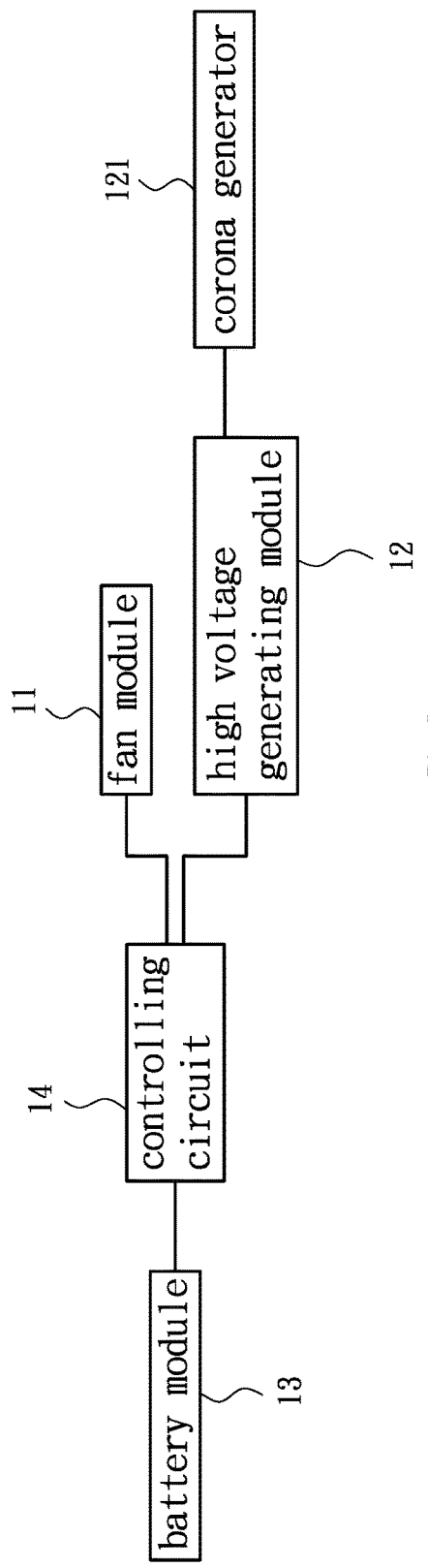
FIG. 3 is a block view of the inner circuit of the device for deodorization and disinfection.

With reference to FIG. 3, a block view of the inner circuit of the device 1 for deodorization and disinfection is shown. To control the operation of the fan module 11 and the high voltage generating module 12, the battery module 13 is connected with the fan module 11 and the high voltage generating module 12 by the controlling circuit 14. So the user can initiate the device 1 for deodorization and disinfection after pressing a switch device 140 (FIG. 1) of the controlling circuit 14. In detail, the controlling circuit 14, for example by using devices such as micro-processor, digital circuit, operational amplifier, can process a signal generated after the switch device 140 is pressed and control the power supply circuit of the fan module 11 and the high voltage generating module 12 after determining that the switch device 140 is pressed (for example through devices such as power transistor, relay) to initiate the fan module 11 and the high voltage generating module 12; and the high voltage generated by the high voltage generating module 12 may be transported to the corona generator 121 provided at the air outlet of the fan module 11 for allowing the corona generator 121 to generate a corona within the discharge area of the corona generator 121 so as to let the output air produce the ozone air by the corona effect, thereby achieving the purpose of initiating the device 1 for deodorization and disinfection.

In another embodiment, axis (body axis) of the aforementioned third supporting portion 103 and axis of the first supporting portion 101 are not overlapped. In another embodiment, a portion volume of the high voltage generating portion 12 is below the first supporting portion 101.

Figure 2:
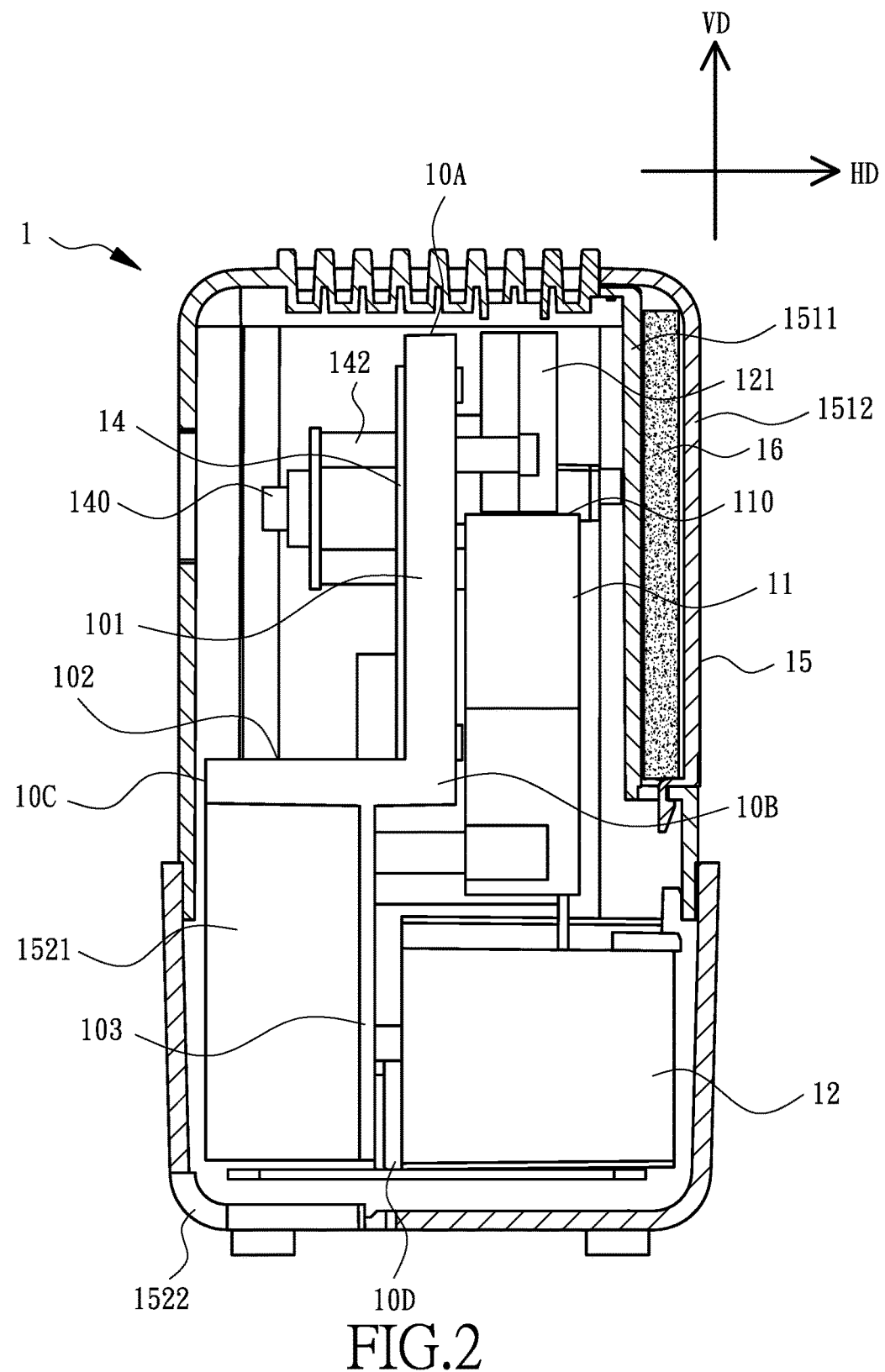
FIG. 2 is a cross section view of the device for deodorization and disinfection.

In another embodiment, transverse section of the holding space is a U shape structure. In another embodiment, the aforementioned device 1 for deodorization and disinfection further comprises a partition plate 1511 (FIG. 2), a filter web 16 and a cover board 1512; the aforementioned partition plate 1511 is connected with the cover body 15 and related to fan blades (not shown, facing one surface of the filter web 16) of the fan module 11. With reference to FIG. 2, the aforementioned filter web 16 is at one side of the partition plate 1511 to make the partition plate 1511 locate between the fan module 11 and the filter web 16; the aforementioned cover board 1512 is at one side of the filter web 16 and embedded at the cover body 15.

In another embodiment, the aforementioned switch device 140 is configured at the other setting plane of the first supporting portion 101. In another embodiment, one portion of the aforementioned switch device 140 of the controlling circuit 14 is embedded at the cover body 15, and a switch sleeve 141 can be configured at the position where the switch device 140 is embedded at the cover body 15 to seal the opening of the aforementioned embedded position. In another embodiment, a pillar 142 is further set up between the switch device 140 and the controlling circuit 14, and the position of the switch device 140 is adjusted by configuring the dimension of the pillar 142.

In another embodiment, the aforementioned cover body 15 further comprises a first body 151 and a second body 152 which can be combined with each other to form a holding space, the supporter 10 is accommodated in the cover body 15 and connected with inside of the cover body 15 through the base 104. More specifically, the supporter 10 is connected with inside of the second body 152. In another embodiment, the aforementioned second body 152 forms a battery holding space 1521 from a bottom to a direction of the holding space so as to contain the battery module 13. In another embodiment, the aforementioned device 1 for deodorization and disinfection also comprises a battery cover 1522 configured at an opening of the battery holding space 1521.

With reference to FIG. 2 again, the present invention, through configuring the geometric structure of supporter 10 and mounting the fan module 11, the high voltage generating module 12, the battery module 13, the controlling circuit 14 in specific positions of the supporter 10, allows the aforementioned modules to distribute along the first axial direction VD of the supporter 10 so as to reduce the volume occupied by the device 1 for deodorization and disinfection in the second axial direction HD and to miniaturize the entire volume of the device 1 for deodorization and disinfection.

After the user presses the switch device 140 (FIG. 1) of the controlling circuit 14 to power the controlling circuit 14, the controlling circuit 14 may supply the power from the battery module 13 to the fan module 11 and the high voltage generating module 12 for triggering operation; and after the fan module 11 operates, the air may be allowed to flow orderly through the cover board 1512, the filter web 16, the fan blades of the fan module 11, the air outlet 110 and the opening of the first body 151, at this moment, a high voltage (e.g. 5 kv to 25 kv) generated by the high voltage generating module 12 may let the air produce and output ozone air through the air outlet 110 mounted with the corona generator 121.

Figure 4:
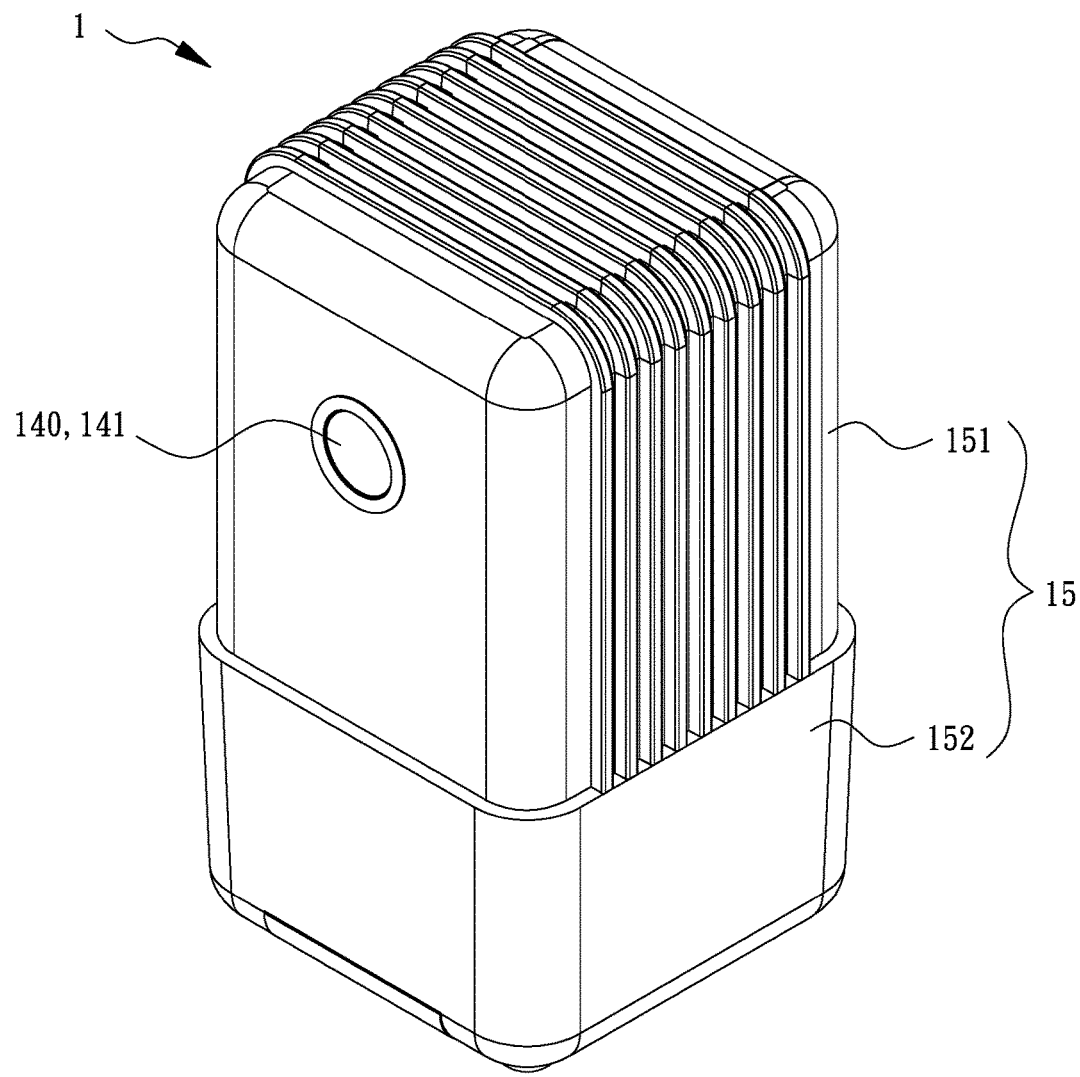
FIG. 4 is a stereoscopic view of the device for deodorization and disinfection.
Figure 5:
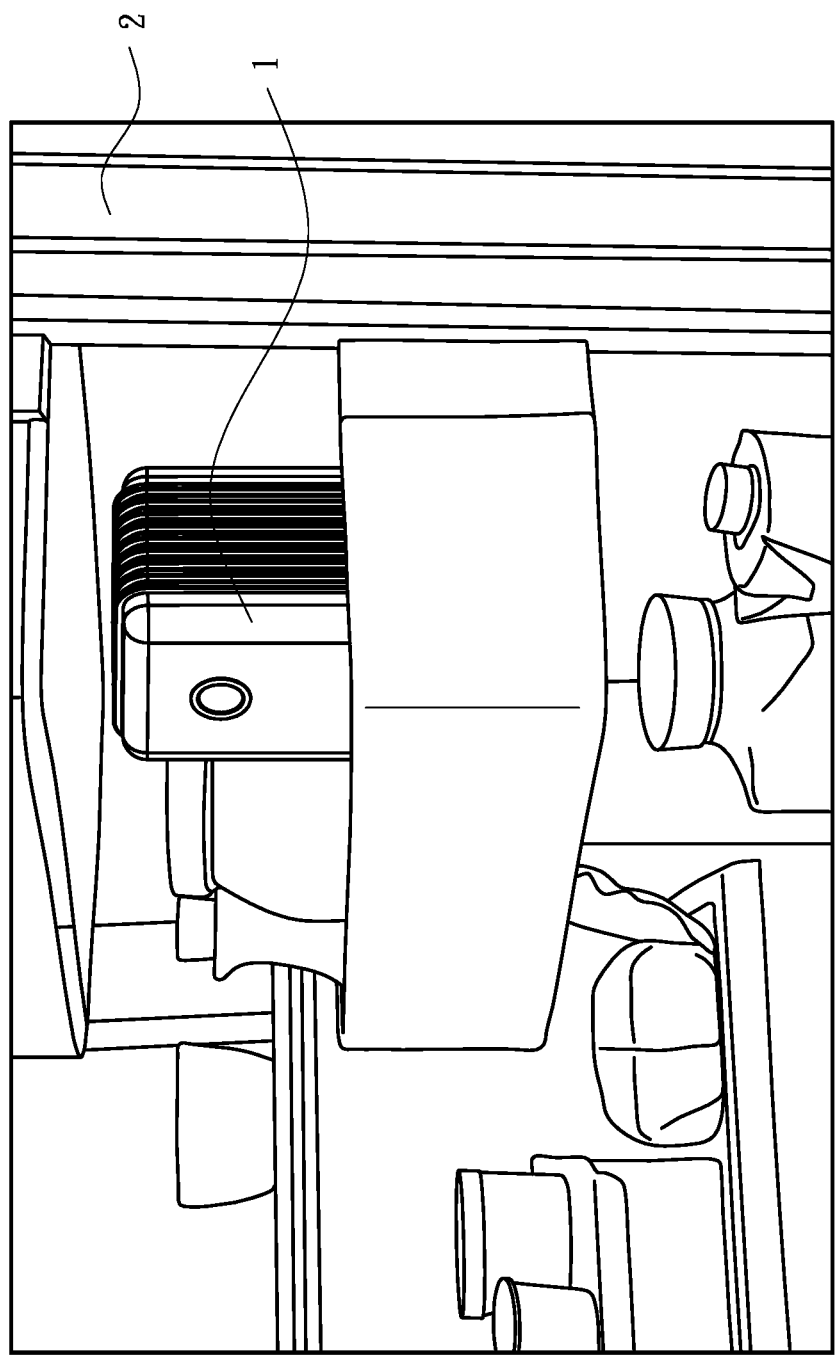
FIG. 5 is a view of a setting environment of the device for deodorization and disinfection.

With reference to FIG. 4, a stereoscopic view of the device 1 for deodorization and disinfection is shown. With reference to FIG. 5, a view of a setting environment of the device 1 for deodorization and disinfection is shown. Since the device 1 for deodorization and disinfection of the present invention effective reduce the volume by configuring the positions of the inner modules thereof and is powered by the battery module 13 contained therein, compared with conventional ozone generator, the device 1 for deodorization and disinfection of the present invention can be placed in an environment with a more narrow space or an environment where there is no power supply (e.g. In a refrigerator 2 in FIG. 5 or a wardrobe).

In addition, the device 1 for deodorization and disinfection of the present invention attaching properly the fan module 11, the high voltage generating module 12, the battery module 13 and the controlling circuit 14 on the supporter 10 can effectively reduce the entire volume of the aforementioned devices and the need to attach on the cover body 15, thus a flexible operation space on the design of the cover body 15 is conferred to the user for making the modeling of the cover body 15 be more diverse and have more product competitiveness.

The above disclosure is related to the detailed technical contents and inventive features thereof. People skilled in this field may proceed with a variety of modifications and replacements based on the disclosures and suggestions of the invention as described without departing from the characteristics thereof.

Nevertheless, although such modifications and replacements are not fully disclosed in the above descriptions, they have substantially been covered in the following claims as appended.

What is claimed is:

1. A device for deodorization and disinfection, comprising:
   a supporter including a first supporting portion, a second supporting portion, a third supporting portion, and a base, wherein one end of the first supporting portion connected with the second supporting portion to form a first angle, and one part of the second supporting portion connected the third supporting portion to form a second angle, one end of the third supporting portion connected with the base;
   a fan module attached to a setting plane of the first supporting portion;
   a high voltage generating module configured at a setting plane of the third supporting portion and below the fan module, wherein a corona generator of the high voltage generating module is configured at an air outlet of the fan module;
   a battery module connected with the fan module and the high voltage module, wherein the battery module is configured at a holding space formed by the second supporting portion and the third supporting portion;
   a controlling circuit electrically connected with the fan module, the high voltage generating module, and the battery module so as to configure an operation of the fan module and the high voltage generating module;
   a cover body configured to cover the supporter, the fan module, the high voltage generating module, the controlling circuit, and the battery module;
   a partition plate, connected with the cover body and related to fan blades of the fan module;
   a filter web, configured at one side of the partition plate to make the partition plate locate between the fan module and the filter web;
   a cover board, configured at one side of the filter web and embedded at the cover body;
   wherein the cover body further comprises a first body and a second body which can be combined with each other;
   wherein the supporter is accommodated in the cover body and connected with inside of the cover body through the base; and
   wherein the axis of the third supporting portion and axis of the first supporting portion are not overlapped.

2. The device as claimed in claim 1, wherein a portion volume of the high voltage generating portion below the first supporting portion.

3. The device as claimed in claim 1, wherein transverse section of the holding space is a U shape structure.

4. The device as claimed in claim 1, wherein a switch device of the controlling circuit is configured at the other setting plane of the first supporting portion.

5. The device as claimed in claim 4, wherein one portion of the switch device is embedded at the cover body.

6. The device as claimed in claim 1, wherein the second body forms a battery holding space from a bottom to a direction of inner of the cover body so as to contain the battery module.

7. The device as claimed in claim 1, wherein the device further comprises a battery cover configured at an opening of the battery holding space.

* * * * *